United States Patent [19]

Watkins

[11] Patent Number: 5,027,443
[45] Date of Patent: Jul. 2, 1991

[54] COMPOSITE FLEXIBLE GOGGLE WITH RIGID LENS SUPPORT

[75] Inventor: Willis T. Watkins, Kansas City, Mo.

[73] Assignee: Parmelee Industries, Inc., Lenexa, Kans.

[21] Appl. No.: 350,947

[22] Filed: May 12, 1989

[51] Int. Cl.⁵ ............................................. A61F 9/02
[52] U.S. Cl. .......................................... 2/437; 2/441; 2/447
[58] Field of Search ................... 2/439, 440, 441, 443, 2/452, 428, 430, 431, 432, 434, 436, 437, 447

[56] References Cited

U.S. PATENT DOCUMENTS

| | | | |
|---|---|---|---|
| 835,828 | 11/1906 | Meyrowitz | 2/437 |
| 1,518,407 | 12/1924 | King | 2/443 |
| 2,388,205 | 10/1945 | Berheim et al. | 2/441 |
| 2,612,639 | 10/1952 | Christensen et al. | 2/436 |
| 2,715,223 | 8/1955 | Stegeman et al. | 2/441 |
| 2,877,463 | 3/1959 | Watkins | 2/436 |
| 3,000,011 | 9/1961 | Sterne et al. | 2/436 |
| 3,031,675 | 5/1962 | Dubach | 2/436 |
| 3,336,599 | 8/1967 | Gatti et al. | 2/428 |
| 3,638,240 | 2/1972 | Militello | 2/437 |
| 3,705,760 | 12/1972 | Langendorfer et al. | 2/447 |
| 3,708,224 | 1/1973 | Lindblom | 2/436 |
| 3,896,496 | 7/1975 | Leblanc et al. | 2/439 |
| 4,087,865 | 5/1978 | Garofalo | 2/428 |
| 4,171,543 | 10/1979 | Cressi | 2/428 |
| 4,264,988 | 5/1981 | Specht | 2/431 |
| 4,447,914 | 5/1984 | Jannard | 2/432 |
| 4,556,995 | 12/1985 | Yamamoto | 2/439 |
| 4,670,914 | 6/1987 | Harris | 2/436 |
| 4,689,838 | 9/1987 | Angermann et al. | 2/441 |
| 4,707,863 | 11/1987 | McNeal | 2/436 |

OTHER PUBLICATIONS

American National Standard 287.1-1979.

Primary Examiner—Peter Nerbun
Attorney, Agent, or Firm—Hovey, Williams, Tommons & Collins

[57] ABSTRACT

Eye protective goggles for protecting a wearer'2 eyes from particulate matter in the air includes a goggles body and a lens support fixedly secured to the body. The lens support includes a circumferential lens fitting groove of predetermined shape and is constructed of a material that is hard and rigid relative to the goggles body. An eye protective lens including a circumferential edge having a shape corresponding to the predetermined shape of the fitting groove is removably attached to the lens support by snap-fit receipt of the circumferenital edge of the lens in the fitting groove. A method of constructing eye protective goggles is also disclosed and includes athe steps of aligning a hard rigid lens support with a relatively soft flexbile goggles body by passing a plurality of tabs of the lens support through a corresponding plurality of slots of the goggles body, and securing the tabs in position relative to the slots so that the tabs are prevented from being withdrawn therefrom. Thereafter, a removable lens may be snap-fit into a fitting groove of the lens support.

14 Claims, 2 Drawing Sheets

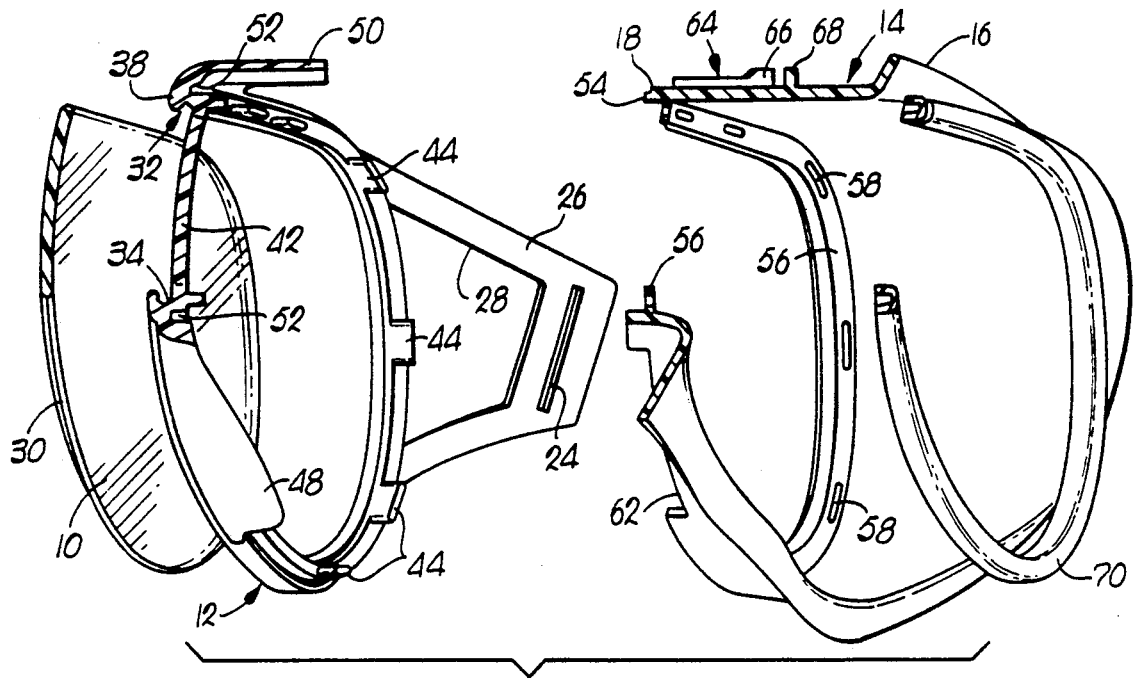
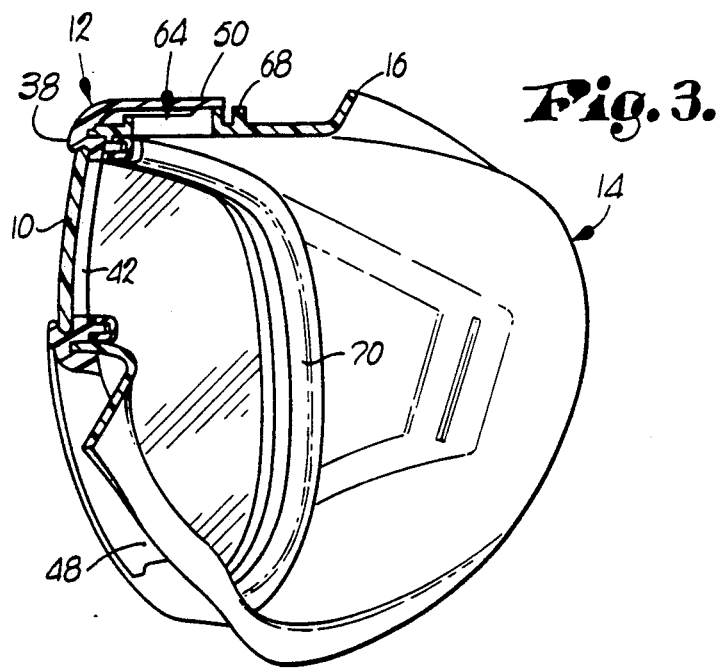
Fig. 4.
Fig. 3.
Fig. 9.
Fig. 8.
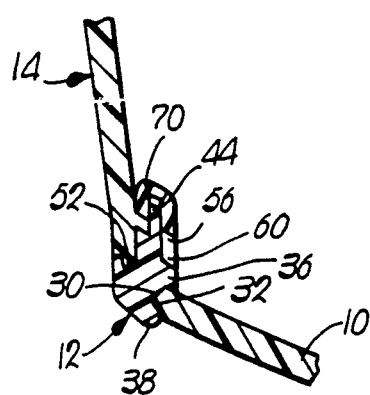
Fig. 7.

COMPOSITE FLEXIBLE GOGGLE WITH RIGID LENS SUPPORT

BACKGROUND OF THE INVENTION

1. Field of the Invention

The present invention relates generally to goggles and, more particularly, to a composite flexible goggles structure having a rigid lens support which provides impact protection to the wearer while permitting replacement of the lens.

2. Discussion of the prior Art

Eye and face protectors are widely used in industry and schools to protect the eyes and faces of craftsmen from flying particulate matter in the air as well as from chemical splashes that may occur in an industrial or laboratory environment. Many different known devices exist which provide various types of protection depending on the range of dangerous hazards encountered in any one setting. Selection charts are published which illustrate the different types of protection available and set forth recommendations as to which of the protective devices is most suitable for a given work environment. An example of such a selection chart is shown in FIG. 8 of *American National Standard* Z87.1-1979, published by the American National Safety Institute.

One known type of protective eye goggles is constructed of a soft flexible fitting goggles body having a lens permanently affixed thereto by means of a sealing fit between the lens and the goggles body. Several advantages are realized by this construction. For example, because of the flexible construction of the goggles body, the goggles conform to the face of the user so as to provide a comfortable fit. Further, the goggles may be constructed relatively inexpensively due to the simplicity of the construction.

However, this known flexible fitting goggles design suffers from several drawbacks. For example, because the flexible goggles body is used as a mounting point for a headband which is provided to retain the goggles on the head of the user, uneven pressure may be exerted on the user's face through the pulling action of the band at the sides of the goggles. This pulling action may cause pressure points to develop on the user's face thus causing discomfort. In addition, in order to secure the lens on the goggles body of the known device, it has in the past been necessary to permanently fix the lens on the goggles body or to employ a lens that has tabs or hooks which permit the lens to be secured to the flexible goggles body. Thus, replacement of the lens is made either impossible or difficult in the known devices by the lens being connected directly to the soft goggles body.

Another feature common in known goggles constructions is the provision of ventilation holes in the sides and top of the goggles body. These ventilation holes may or may not be provided with means for preventing splashed liquids from entering the goggles, and are arranged to permit air flow through the goggles such that fogging does not occur. However, it has been found that many of these ventilation systems are not satisfactory and that some fogging may occur even in the presence of such systems.

OBJECTS AND SUMMARY OF THE INVENTION

It is an object of the present invention to provide an eye protective goggles construction which includes a soft flexible goggles body that will conform to the face of the user, while providing a rigid lens support that is attached to the goggles body and that removably retains the lens on the goggles to permit simplified replacement of the lens.

Further, it is an object of the invention to provide a goggles construction in which a headband may be reliably supported on the goggles in such a manner as to evenly distribute the pulling force of the headband around the circumference of the goggles, thus relieving pressure points on the face of the user.

Another object of the invention is to provide eye protective goggles having a ventilation system that creates a chimney effect around the nose of the user, which is where a substantial amount of heat is generated, such that cool air is drawn into the goggles adjacent the nose of the user and passes up through the goggles toward an upper ventilation arrangement.

In addition to these objects, yet another object of the invention is to provide a method of constructing eye protective goggles which enables a rigid lens support to be attached to a soft flexible goggles body and which permits a lens to be removably snap-fit on the rigid lens support.

According to the present invention, eye protective goggles comprise a goggles body and a lens support fixedly secured to the goggles body and constructed of a material that is hard and rigid relative to the goggles body. The lens support includes a circumferential lens fitting groove of predetermined shape, and an eye protective lens is provided including a circumferential edge having a shape corresponding to the predetermined shape of the fitting groove. The lens is removably attached to the lens support by snap-fit receipt of the circumferential edge of the lens in the fitting groove.

The lens support preferably includes a lens retaining wall and a lens retaining lip disposed forward of and spaced from the retaining wall, with the fitting groove extending between the retaining wall and the retaining lip. Further, the fitting groove is to be of a depth which varies along the circumference thereof to define a deep groove portion and a shallow groove portion, the deep groove portion being provided to permit a portion of the circumferential edge of the lens to be inserted therein during attachment of the lens to the lens support to enable the remaining portion of the circumferential edge to pass over the retaining lip and into the shallow portion of the fitting groove.

In addition, a headband may be provided along with band attachment means on the lens support for attaching the headband to the goggles. A ventilation means is also preferably provided which includes a lower ventilation arrangement disposed in the nose bridge and an upper ventilation arrangement vertically displaced from the lower ventilation arrangement so that air passing into the lower ventilation arrangement passes upward through the goggles to the upper ventilation arrangement.

A method of constructing eye protective goggles in accordance with the invention includes the steps of aligning a hard rigid lens support with a relatively soft flexible goggles body by passing a plurality of tabs of the lens support through a corresponding plurality of slots of the goggles body, securing the tabs in position relative to the slots so that the tabs are prevented from being withdrawn therefrom, and snap-fitting a removable lens into a fitting groove of the lens support.

BRIEF DESCRIPTION OF THE DRAWING FIGURES

A preferred embodiment of the invention is described in detail below with reference to the attached drawing figures, wherein:

FIG. 3 is a sectional view of the goggles shown in FIG. 1, taken along line 3-3;

FIG. 4 is an exploded view of the goggles section illustrated in FIG. 3;

FIG. 7 is a sectional view of an upper ventilation segment of the flexible goggles body;

FIG. 8 is a sectional view taken along line 8—8 of FIG. 1; and

FIG. 9 is a sectional view taken along line 9—9 of FIG. 1.

DETAILED DESCRIPTION OF THE PREFERRED EMBODIMENT

Figure 1:
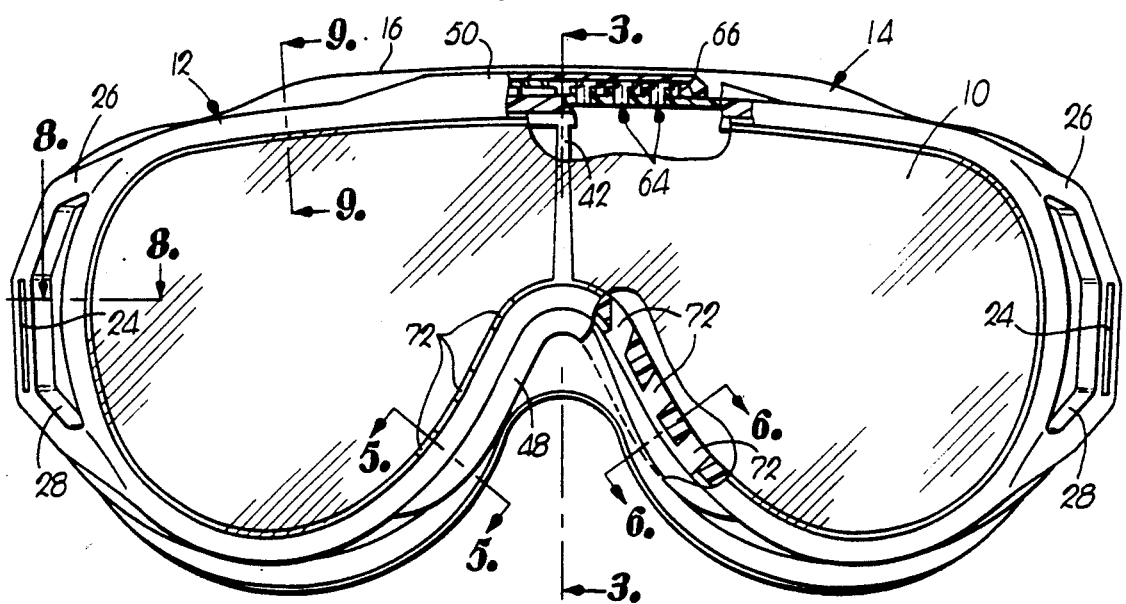
FIG. 1 is a front view, partially cut away, of goggles constructed in accordance with the present invention.

A pair of eye protective goggles constructed in accordance with a preferred embodiment of the invention are illustrated in FIG. 1. As shown, the goggles include three major components; a lens 10, a rigid lens support 12 and a soft flexible goggles body 14.

The goggles are constructed in a shape presenting a clean design enabling substantially unrestricted forward and peripheral vision to a user, and are sized to permit the goggles to be worn either directly over the face of the user or over the top of prescription spectacles when vision correction is required. Further, as described below, a ventilation system is provided which includes a lower ventilation arrangement and an upper ventilation arrangement.

Figure 2:
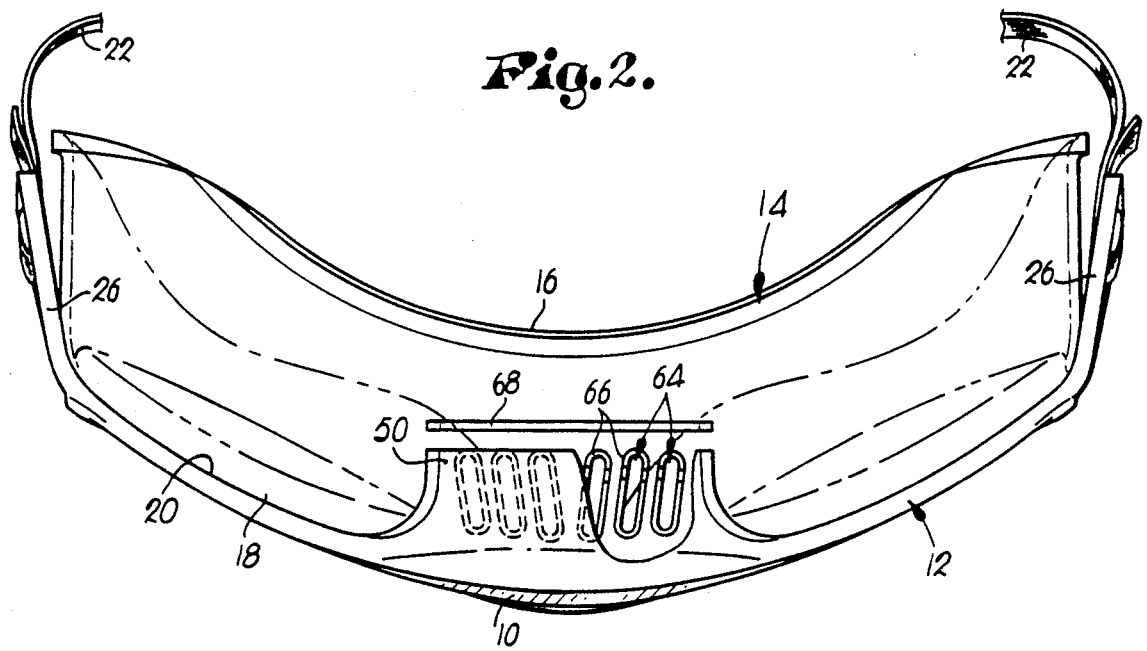
FIG. 2 is a top view, partially cut away, of the goggles shown in FIG. 1.

Turning to FIG. 2, it is seen that the soft flexible goggles body 14 is formed to fit comfortably over the face of the user, and includes a rear edge 16 adapted to contact and press against the user's face in the region of the forehead, cheeks and nose. A forward edge 18 of the flexible body 14 is attached to the rigid lens support 12 and mates with a rear surface 20 of the support 12 in a manner described below.

A headband 22 is provided on the goggles and is attached to the goggles through two slots 24 formed in a pair of laterally disposed extending portions 26 of the lens support 12. These extending portions 26 are constructed of the same rigid material as the lens support 12 and extend rearward thereof. Each of the extending portions 26 also includes a band receiving opening 28 adjacent the slot 24 in which the band is received for fastening. By attaching the band 22 to the rigid lens support 12 of the goggles, the pulling force exerted by the band on the goggles is distributed by the rigid lens support 12 along the entire width of the goggles, thus reducing the amount of pressure exerted on the face of the user at the sides of the goggles. In addition, because the extending portions 26 of the lens support 12 are made of the same material as the support, the extending portions do not become significantly disfigured when the ends of the band 22 are pulled during adjustment thereof. Such disfigurement occurs in known devices of the type described above and causes difficulty in making adjustments in the length of the headband by impeding movement of the headband relative to the goggles body. By attaching the headband 22 to the rigid support 12, adjustment of the band may be carried out easily and quickly by simply pulling on the loose ends of the band 22.

The manner in which the major components of the goggles are assembled is shown in FIG. 3, and an exploded view further illustrating the separate components of the goggles is provided in FIG. 4. In order to describe the preferred constructions of each of the components of the goggles, reference is made primarily to FIG. 4.

As shown in this figure, the lens 10 employed in the preferred embodiment is a single piece lens having an overall spherical contour shape which permits a reduction in the size and weight of the goggles by presenting a lens contoured to follow the facial shape of a person wearing the goggles, and thus reducing the amount of material that must be used in the goggles body 14 to close off the lateral sides of the goggles between the lens and the face of a person wearing the goggles. The lens 10 is constructed of a material of sufficient hardness to resist breaking or puncture upon experiencing an impact during use, and is preferably resistant to chemical erosion as well. For example, the lens may be constructed of a polycarbonate having a hardness of approximately 70 Rockwell M.

The lens 10 extends across substantially the entire width of the goggles to provide the maximum field of vision possible, and includes a cutout portion intermediate the sides thereof defining a nose bridge. The lens is also provided with a circumferential edge 30 extending therearound which is beveled, as shown in FIG. 9, to present a generally chevron-shaped cross section around the circumference of the lens 10. As described in more detail below, the chevron-shaped edge 30 of the lens facilitates the snap-in, snap-out replacement of the lens while providing reliable retention of the lens in the lens support 12 during impacts encountered during use.

Immediately rearward of the lens 10 is the lens support 12 which is constructed of a material that is hard relative to the material of the lens. For example, in the preferred embodiment, the lens support 12 may be constructed of a polyamide having a hardness of approximately 85 Shore D, or roughly 93 Rockwell M. By employing such a material in the lens support, a secure fit between the lens 10 and lens support 12 is ensured and it is possible to retain the lens in the support during impact to the lens, while permitting relatively easy snap-in, snap-out replacement thereof.

A radially inward directed circumferential lens fitting groove 32 extends around the inner periphery of the lens support 12. The fitting groove 32 is shaped to receive the circumferential edge 30 of the lens 10 and to hold the lens securely in place during normal use of the goggles. A bottom wall of the fitting groove is defined between a rear lens retaining wall 36 and a forward lens retaining lip 38, both of which extend along the entire length of the groove 32 at a constant spaced distance from one another approximately equal to the thickness of the lens 10. The bottom wall is formed by a pair of angled surfaces which are shaped to receive the chevron-shaped edge 30 of the lens 10 when the lens is properly attached to the lens support 12.

The retaining lip 38 is of a curved or semi-cylindrical cross-sectional shape presenting a smooth curved surface to the fitting groove 32 which extends radially inward beyond the bottom wall of the groove 32 by a short distance so that the lip 38 retains the lens 10 in place in the groove during normal use of the goggles. The rear retaining wall 36 includes a flat wall surface 40 adjacent the fitting groove 32 which extends radially inward beyond the bottom wall of the fitting groove 32 by a distance somewhat greater than does the retaining lip 38. By constructing the retaining wall 36 in this manner, the lens 10 is prevented from being pressed rearward past the groove 32 into the interior of the goggles either during snap-in attachment of the lens to the lens support, or upon the lens experiencing an impact during normal use of the goggles.

A vertical brace member 42 is also provided on the lens support 12 at a position intermediate the sides of the goggles and extends between the rear retaining wall 36 adjacent the nose bridge and the upper segment of the retaining wall, such that the member 42 bisects the circumference of the fitting groove 32. The brace member 42 stiffens the lens support 12 and prevents the lens 10 from being forced inward of the goggles past the rear retaining wall 36 in addition to preventing the fitting groove 32 from being excessively deformed to the point of permitting unwanted relative movement between the lens and the lens support either during insertion of the lens into the fitting groove or during normal use of the goggles.

A plurality of tongue elements or tabs 44 are formed in the lens support 12 and extend from a rear surface 46 of the retaining wall 36. The tabs 44 are spaced around the circumference of the retaining wall 36 and are used in a manner described below to connect the lens support 12 to the soft flexible goggles body 14. A ventilation shield 48 and ventilation hood 50 are also formed in the lens support 12 and serve to prevent splashed fluids and the like from entering the lower and upper ventilation arrangements.

The lens support 12 is further provided with a body receiving groove 52 which extends along the entire circumference of the lens support 12 and is disposed radially outward of the tabs 44. The groove 52 is adapted to mate with a corresponding stepped surface 54 of the goggles body 14, described below, to position and retain the lens support 12 on the goggles body 14.

The goggles body 14 is constructed from a material that is flexible and soft relative to the lens support 12 and the lens 10, and which may be transparent to increase the peripheral range of vision through the goggles. In its preferred form, the goggles body 14 is made of a PVC material having a hardness of 70-85 Shore A. The goggles body 14 includes a single generally tubular component extending between the front edge 18, adapted to be attached to the lens support, and the rear edge 16 adapted to engage the face of a person wearing the goggles. The front edge 18 of the body 14 includes the stepped surface 54 which mates with the groove 52 in the lens support 12 so that, upon assembly of the goggles, the lens support 12 may be accurately positioned relative to the flexible goggles body 14 and a sealing fit may be provided between the two components. A radially inward directed flange 56 is disposed on the body 14 a short distance to the rear of the front edge 18 of the body 14. This flange 56 includes a plurality of slots 58 aligned with the tabs 44 of the lens support 12, the slots being adapted to receive the tabs during assembly of the goggles. A further forward extending lip 60 may be provided at the radially inner edge of the flange 56 to provide further locating means on the goggles body 14 for positioning the lens support 12 relative to the body during assembly thereof.

A pair of recesses 62 are formed in the goggles body 14 adjacent the sides of the nose bridge and serve as a passage for the lower ventilation arrangement described below. These recesses 62 are aligned with the shield 48 on the lens support 12 so that the recesses 62 are shielded from exposure to fluids being splashed about the face of the person wearing the goggles. Upper air passages 64 are also provided on the goggles body 14 for permitting air to escape from the top of the goggles. Each of these upper passages 64 is surrounded by a vertically extending wall 66 which impedes fluid from pouring into the passages from outside the goggles. A dam 68 is also formed in the top of the goggles body 14 and extends along the width of all of the upper passages 64 in order to provide further means for blocking the flow of fluids into the passages.

A retaining ring 70 is illustrated in FIG. 4, which is used as a preferred means for fastening the tabs 44 in place relative to the goggles body 14 during assembly of the goggles. This retaining ring 70 is constructed of one or more pieces and includes either a slot or a number of recesses therein sized to receive one or more of the tabs 44. During construction of the goggles, the tabs 44 of the lens support 12 are guided through the slots 58 on the flange 56 of the goggles body 14 and are fitted in the recesses of the retaining ring 70. The relationship between the tabs 44 of the lens support, the flange 56 of the flexible body 14 and the retaining ring 70 is shown in FIG. 8. The tabs 44 may be retained in the recesses by an suitable means such as by employing a friction fit, heat welding or adhesives. Further, although in the preferred embodiment of the invention the retaining ring 70 is a single piece, it is noted that separate tab retaining elements could be provided in place of the ring, so long as some operable means is provided for securing the tabs 44 in place relative to the goggles body 14. In FIG. 9, the relationship between the lens support 12, the goggles body 14 and the retaining ring 70 is illustrated at a region of the lens support which is between two of the tabs 44.

With reference to FIG. 1, the lower ventilation arrangement includes a plurality of ventilation openings 72 disposed on each side of the nose bridge of the goggles. These openings 72 coincide with the recesses 62 in the goggles body, and permit air to enter the interior of the goggles adjacent the nose of the person wearing them to ventilate that region of the person's face in which a substantial amount of heat is generated and at which fogging frequently occurs. As the air enters these ventilation openings 72, heat is transferred to the air causing the air to rise toward the top of the goggles and out the upper ventilation arrangement. This rising exiting air also draws further cool air into the lower openings so that a chimney effect is created which continues to ventilate the interior of the goggles.

Figure 5:
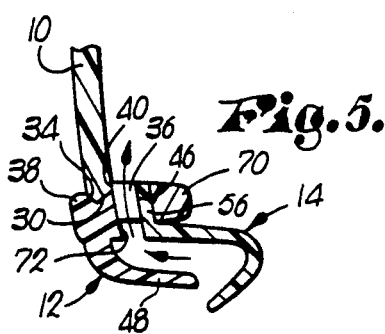
FIG. 5 is a sectional view taken along line 5—5 of FIG. 1.
Figure 6:
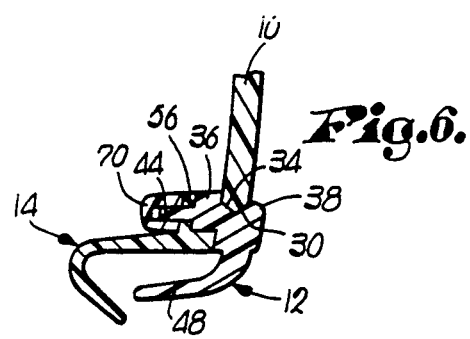
FIG. 6 is a sectional view taken along line 6—6 of FIG. 1.

One of the lower ventilation openings 72 is illustrated in FIG. 5, and is formed between the lens support 12 and the soft goggles body 14 by a radially extending slot in the rear retaining wall 36 of the lens support. In the regions of the lower ventilation arrangement between each of the lower ventilation openings 72, the retaining wall may be provided with a tab 44, such as is shown in FIG. 6, which may be secured in place relative to the goggles body 14 by attachment to the retaining ring 70.

The shield 48 of the lens support 12 is disposed in front of the lower ventilation openings 72 to prevent fluids from being splashed directly into the openings, and a flexible nose bridge of the goggles body 14 extends forward of the openings to aid the shield 48 in protecting the openings from exposure to fluids.

As mentioned, air passing up through the goggles exits the goggles through the upper ventilation arrangement. This upper arrangement is formed by the upper passages 64, the vertically extending walls 66 surrounding the passages, and the dam 68, as illustrated in FIG. 7, along with the hood 50 of the lens support 12. The lens support hood 50 extends over the vertically extending walls 66 and contacts the upper surface of each of the walls adjacent the rear end thereof where the height is somewhat greater than at the front end thereof. Normally, as can be seen from FIG. 3, air is permitted to escape from the goggles through the upper passages 64 by passing up over the vertically extending walls 66 along the forward region of the walls which are of reduced height as compared with the rear ends of the walls. Once the air has passed over the walls 66, it flows beneath the hood 50 to the open rear side thereof where it is released to the atmosphere.

When fluid is splashed onto the top of the goggles, it is initially prevented from entering the upper passages 64 by the dam 68 which blocks the flow of the fluid and redirects the fluid to the sides of the goggles. Any fluid which gets over the dam 68 and under the hood 50 of the lens support 12 washes up against the sides of the vertical walls 66 and is also prevented from entering the passages 64. Thus, although the upper passages extend vertically through the top of the goggles body, means are provided for preventing fluid from entering the passages.

The manner in which the goggles are constructed is as follows. The initial step in the assembly process involves aligning the lens support 12 with the goggles body 14 such that the tabs 44 of the support line up with the corresponding slots 58 in the flange 56, and the stepped edge 18 of the body lines up with the groove 52 of the support 12. The two components are then pressed together so that the tabs 44 pass through the slots 58 and the stepped edge 18 of the body mates with the groove 52 of the support.

After the support 12 and body 14 have been pressed together, the retaining ring 70 is positioned on the tabs 44 of the support and pressed up against the flange 56 of the body such that the retaining ring presses and holds the support 12 against the body 14. As previously mentioned, the tabs 44 may be secured in the recesses of the retaining ring 70 in any of a number of different ways. For example, by sizing the recesses of the retaining ring slightly smaller than the tabs, the tabs may be forced into the recesses to provide a friction fit between the tabs 44 and the ring 70. Alternately, an adhesive may be inserted between the tabs and the ring, or heat treatment of the retaining ring may be employed to heat seal the tabs to the ring. Ultrasonic vibration could also be used to fuse the tabs to the ring.

Although tabs are illustrated in the preferred embodiment of the invention, it is noted that other means may be provided for connecting the lens support to the goggles body. For example, pawl-type hooks or ridges may be employed which would permit the lens support to be pressed into contact with the goggles body while preventing reverse movement of the support away from the body, or flanges could be provided on the lens support during an ultrasonic welding or heat treatment process such that the lens support and goggles body could be deformed to secure the lens support in place on the goggles body. Further, a single tongue may be provided on the support 12 in place of the tabs 44, which can be deformed by a heating or ultrasonic welding process to secure the lens support to the goggles body. In this construction, the goggles body may include a small flange or lip in place of the flange 56 and slots 58 of the illustrated embodiment, such that the lip is gripped by the tongue once the tongue is deformed.

Regardless of the method used to secure the lens support to the goggles body, once the lens support 12 is secure, the lens 10 may be inserted into the fitting groove 32 to complete the assembly. As shown in FIG. 3, the fitting groove is not of a constant depth, but rather includes a section 34 adjacent the bottom of the brace member 42 which is deeper than the remaining groove. By providing this deep section 34 in the groove, when the lower edge of the lens is initially inserted into the lower portion of the fitting groove, the section of the lens adjacent the brace member 42 may be pressed down into the deep groove section 34 to a depth sufficient to permit the upper edge of the lens to be pressed over the retaining lip 38 of the lens support 12 and into the fitting groove 32. Thereafter, the slight resilience of the lens and lens support about the circumference of the fitting groove biases the edge 30 everywhere along the groove except in the deep section adjacent the member 42. The hood 50 on the lens support may be employed as a lever during insertion of a lens into the goggles by pressing down on the hood while forcing the edge of the lens over the retaining lip into the fitting groove. When the hood is compressed, the retaining lip along the top of the lens support is biased slightly upward and forward of the goggles so as to permit the lens to pass into the groove.

When it is desired to replace the lens, either because the lens has become dirty or has been scratched, it is only necessary to force the upper edge of the lens out of the fitting groove by pressing forward and downward on the lens until the lens snaps out of the groove. Thereafter, the old lens may be disposed of and a new or different lens may be inserted in the goggles.

Although the invention has been described with reference to a preferred embodiment, it is noted that substitutions may be made and equivalents employed herein without departing from the scope of the invention as set forth in the claims.

What is claimed is:

1. Eye protective goggles comprising:

a goggles body;

a lens support fixedly secured to the goggles body and including a lens fitting groove of predetermined shape, a lens retaining wall, and a lens retaining lip disposed forward of and spaced from the retaining wall, the fitting groove extending between the retaining wall and the retaining lip, the lens support being constructed of a material that is hard relative to the goggles body; and an eye protective lens including a circumferential edge having a shape corresponding to the shape of the fitting groove, the lens being removably attached to the lens support by snap-fit receipt of the circumferential edge of the lens in the fitting groove, the fitting groove having a depth which varies along the circumference thereof to define a deep groove portion and a shallow groove portion, the deep groove portion being provided to permit a segment of the circumferential edge of the lens to be inserted therein during attachment of the lens to the lens support to enable the remaining portion of the circumferential edge to pass over the retaining lip and into the shallow portion of the fitting groove.

2. The goggles of claim 1, wherein the eye protective lens is formed of a spherical contour shape.

3. The goggles of claim 1, wherein the lens support material has a hardness of approximately 85 Shore D and the goggles body is constructed of a body material having a hardness of approximately 70-80 Shore A.

4. The goggles of claim 1, further comprising a headband adapted to hold the goggles on the head of a wearer, the lens support further including band attachment means for attaching the headband to the goggles.

5. Eye protective goggles comprising:
a goggles body;
a lens support fixedly secured to the goggles body and including a lens fitting groove of predetermined shape, a lens retaining wall, and a lens retaining lip disposed forward of and spaced from the retaining wall, the fitting groove extending between the retaining wall and the retaining lip, the lens support being constructed of a material that is hard relative to the goggles body and including a plurality of tabs extending rearward of the lens retaining wall, the goggles body having a circumferential flange extending along the lens retaining wall, the circumferential flange including a plurality of slots through which the tabs extend, the goggles further comprising tab securing means for preventing the tabs from being withdrawn from the slots such that the lens support is fixedly secured to the goggles body; and
an eye protective lens including a circumferential edge having a shape corresponding to the shape of the fitting groove, the lens being removably attached to the lens support by snap-fit receipt of the circumferential edge of the lens in the fitting groove.

6. The goggles of claim 8, wherein the tab securing means includes a tab securing ring having a plurality of tab receiving holes sized to receive the tabs, the goggles further comprising means for retaining the tabs in the tab receiving holes.

7. The goggles of claim 1, further comprising:
a nose bridge defined by the goggles body, the lens support and the lens; and
ventilation means for permitting air to flow through the goggles, the ventilation means including a lower ventilation arrangement disposed in the nose bridge and an upper ventilation arrangement vertically displaced from the lower ventilation arrangement so that air passing into the lower ventilation arrangement passes upward through the goggles to the upper ventilation arrangement.

8. The goggles of claim 7, wherein both the upper and lower ventilation arrangements include splash prevention means for inhibiting fluids from entering the goggles through the ventilation arrangements.

9. The goggles of claim 5, wherein the eye protective lens is formed of a spherical contour shape.

10. The goggles of claim 5, wherein the lens support material has a hardness of approximately 85 Shore D and the goggles body is constructed of a body material having a hardness of approximately 70-80 Shore A.

11. The goggles of claim 5, further comprising a headband adapted to hold the goggles on the head of a wearer, the lens support further including band attachment means for attaching the headband to the goggles.

12. A method of constructing eye protective goggles comprising the steps of:
aligning a hard lens support with a relatively soft flexible goggles body by aligning at least one tongue of the lens support with at least one corresponding lip of the goggles body;
securing the at least one tongue in position relative to the at least one lip so that the at least one tongue is prevented from being withdrawn therefrom;
snap-fitting a removable lens into a fitting groove of the lens support by inserting a portion of a circumferential edge of the lens into a deep portion of the fitting groove and passing the remaining portion of the circumferential edge of the lens over a retaining lip of the lens support and into a shallow portion of the fitting groove.

13. A method of constructing eye protective goggles comprising the steps of:
aligning a hard lens support with a relatively soft flexible goggles body by aligning at least one tongue of the lens support with at least one corresponding lip of the goggles body;
securing the at least one tongue in position relative to the at least one lip by press-fitting the at least one tongue into at least one hole of a tab securing ring so that the at least one tongue is prevented from being withdrawn therefrom;
snap-fitting a removable lens into a fitting groove of the lens support.

14. A method of constructing eye protective goggles comprising the steps of:
aligning a hard lens support with a relatively soft flexible goggles body by aligning at least one tongue of the lens support with at least one corresponding lip of the goggles body;
securing the at least one tongue in position relative to the at least one lip by deforming the at least one tongue into a shape which secures the lens support to the goggles body so that the at least one tongue is prevented from being withdrawn therefrom;
snap-fitting a removable lens into a fitting groove of the lens support.

* * * * *